(12) United States Patent
Nguyen

(10) Patent No.: US 9,175,316 B2
(45) Date of Patent: Nov. 3, 2015

(54) EFFICIENT PRODUCTION OF BIOFUELS FROM CELLS CARRYING A METABOLIC-BYPASS GENE CASSETTE

(71) Applicant: Ebio, LLC, Houston, TX (US)

(72) Inventor: Trent Nguyen, Houston, TX (US)

(73) Assignee: Ebio, LLC, Houston, TX (US)

( * ) Notice: Subject to any disclaimer, the term of this patent is extended or adjusted under 35 U.S.C. 154(b) by 0 days.

(21) Appl. No.: 13/694,542

(22) Filed: Dec. 12, 2012

(65) Prior Publication Data

US 2014/0162328 A1 Jun. 12, 2014

(51) Int. Cl.
| | |
|---|---|
| *C12P 7/06* | (2006.01) |
| *C12P 7/40* | (2006.01) |
| *C12N 15/70* | (2006.01) |
| *C12P 5/02* | (2006.01) |
| *C12P 7/04* | (2006.01) |
| *C12P 7/16* | (2006.01) |
| *C12P 7/18* | (2006.01) |
| *C12P 7/28* | (2006.01) |
| *C12P 7/56* | (2006.01) |
| *C12P 7/64* | (2006.01) |
| *C12N 1/38* | (2006.01) |

(52) U.S. Cl.
CPC ... *C12P 7/40* (2013.01); *C12N 1/38* (2013.01); *C12N 15/70* (2013.01); *C12P 5/026* (2013.01); *C12P 7/04* (2013.01); *C12P 7/06* (2013.01); *C12P 7/16* (2013.01); *C12P 7/18* (2013.01); *C12P 7/28* (2013.01); *C12P 7/56* (2013.01); *C12P 7/6409* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 5,231,017 | A * | 7/1993 | Lantero et al. | 435/161 |
| 5,821,093 | A * | 10/1998 | Ingram et al. | 435/161 |
| 7,429,476 | B2 * | 9/2008 | Clarkson et al. | 435/219 |
| 8,039,239 | B2 * | 10/2011 | Reeves | 435/161 |
| 8,623,622 | B2 * | 1/2014 | Srienc et al. | 435/165 |
| 8,716,002 | B2 * | 5/2014 | Yomano et al. | 435/252.3 |
| 2009/0203089 | A1 * | 8/2009 | Kashiyama | 435/105 |
| 2011/0014671 | A1 * | 1/2011 | Serna Saldivar et al. | 435/161 |
| 2011/0104736 | A1 * | 5/2011 | Pronk et al. | 435/29 |
| 2012/0058533 | A1 * | 3/2012 | Biton et al. | 435/161 |
| 2012/0244590 | A1 * | 9/2012 | Lee | 435/161 |
| 2012/0309067 | A1 * | 12/2012 | Matsui et al. | 435/161 |
| 2013/0252301 | A1 * | 9/2013 | Jessen et al. | 435/161 |
| 2013/0288325 | A1 * | 10/2013 | Liao et al. | 435/161 |

* cited by examiner

*Primary Examiner* — Robert Mondesi
*Assistant Examiner* — Richard Ekstrom

(57) ABSTRACT

A process for increasing the production of a glycolytic intermediate and/or an organic compound as defined herein by a cell that is able to express a nucleic acid molecule, wherein the expression of the nucleic acid molecule gives the cell the ability to increase the production of a glycolytic intermediate and/or the organic compound and wherein the carbon substrate is sugar and/or protein.

6 Claims, 4 Drawing Sheets

EFFICIENT PRODUCTION OF BIOFUELS FROM CELLS CARRYING A METABOLIC-BYPASS GENE CASSETTE

CROSS-REFERENCE TO RELATED APPLICATION

This application claims the benefit of provisional patent application Ser. No. 61/570,730 filed 2011 Dec. 14 by the present inventor.

FIELD OF THE INVENTION

The invention relates to a process for increasing the production of a glycolytic intermediate and/or an organic compound as defined herein by a cell that is able to express a nucleic acid molecule, wherein the expression of the nucleic acid molecule gives the cell the ability to increase the production of a glycolytic intermediate such as pyruvate or glyceraldehyde 3-phosphate to produce said organic compound. Further, the invention relates to an *Escherichia coli* cell for use in this process that is able to use protein and/or sugar as a carbon source.

BACKGROUND OF THE INVENTION

The energy-producing organisms such as plants, some algae, and cyanobacteria produce energy not only for themselves but also for almost all other organisms on Earth. The product of photosynthesis is glucose, the immediate energy source of cells. Once photosynthesized, glucose can be used either to make energy for cellular work or converted into complex molecules of starch, oil, and proteins as stored energy, structural components, or molecular machineries. Proteins in cells serve critical functions such as structural components, enzymes, transport proteins, and cellular energy source. The structural components of plant cell wall are made up of 2-10% proteins, and the cell membrane contains 50% proteins. The breakdown of proteins and mobilization of amino acids depend on the physiologic needs of plants under various conditions such as oxidative stress, salinity, seasonal change, and developmental stages.

Plants grown in a medium with high salt concentrations have lower energy levels, are shorter, have smaller biomass, and have a lower protein content in comparison with plants grown in low salt concentrations (Maria et al. 2001). As a case in point, Asish et al. (2005) showed that a salt-sensitive protein SSP-23 degrades at high salt concentration in the mangrove plant species *Bruguiera parviflora*, and the phenomenon is suggestive of a salt tolerance mechanism, which adjusts for the osmolarity difference by releasing the protein's amino acid content. High-salt medium seems to be a catalyst for protein breakdown like the SSP-23 degradation and its amino acid mobilization.

Plants adjust the level of energy utilization according to their developmental needs. During the winter, energy is reserved in the form of starch, proteins, and amino acids, which are derived from glucose photosynthesized during late summer. In the fresh pith of tobacco plant species *Nicotiana tabacum*, which represents a slow-growing tissue much like plants in winter months, 88% of the total cellular amino acids are present in a soluble pool with only 12% incorporated into proteins. Conversely the plant's callus, a rapid outgrowth tissue from growing the pith tissue in an artificial nutrient-rich medium, has only 8% of total amino acids in the soluble pool and 92% in proteins. Further, the most abundant amino acids in the soluble pool are glutamine, asparagine, glutamine, and aspartic acid (Kemp et al. 1972). The amino acid reserve of alanine, arginine, and asparagine comes from the nitrogen fixation of ammonia, probably via glutamine (Menegus et al., 1993). These reserve sources of energy and nitrogen-rich compounds are tapped in the spring when apical growth begins.

During the metabolically-dormant winter, plants do not produce much photosynthesized oxygen that can breakdown cell membrane and, thus, release its protein content. For example, some rhizomes (creeping rootstalks) such as *P. australis, A. calamus*, and *S. lacustris* keep their membranes intact during the winter. The growth condition that begins in the spring provides a sudden surge in oxygen that can damage cell membrane though the process called lipid peroxidation. Then, membrane-bound proteins are released, which provide an amino acid pool as a source for both energy and for making other proteins needed for growth. However, the rootstalk plant species *Iris pseudocorus* produces the anti-oxidant enzyme superoxide dismutase (SOD) during the anoxic winter season for stabilizing the oxidant surge in the spring. For those species that do not produce SOD just before spring, the change in season provides a burst of protein pool as a source of energy for the growth requirement.

Under the oxygen deprivation condition called anoxia, plants arrest oxidative phosphorylation and produce only 2 molecules of ATP during fermentation rather 36 ATP under oxygen-using metabolism. In response to anoxic stress, plants adapt by increasing the ATP production rate (Pasteur Effect) although not totally making up for the energy deficit. Under anoxia, the synthesis of plant proteins is inhibited by the destabilization of the protein-producing machineries of polysomes (Baily-Serres, 1990). Some genes turned on by anoxia are metabolism-specific and include alcohol dehydrogenase, pyruvate decarboxylase, enolase, glucose-6-phosphate isomerase, glyceraldehyde-3-phosphate dehydrogenase, lactate dehydrogenase, and sucrose synthase (Sachs et al. 1996), and these enzymes speed up the conversion of energy substrates into energy molecules to compensate for the lack of an energetic state during anoxia. With limited protein synthesis during anoxia, growth is impeded in most plant tissues except for the seed leaf (coleoptile) of germinating rice seedlings, which is unique in its fast growing rate under anoxia while other organs of the seedlings are inhibited from growing (Vartapetian et al., 1978). The energy for the coleoptile growth may come from the rice seed covering layer aleurone, which increases its soluble protein pool in addition to its protease concentrations during germination (Miyuki et al., 2002). With the intact rice seed containing 7-9% protein content, the significant pool of amino acids can provide the initial substrates for conversion into sugar by gluconeogenesis.

The growth-inhibiting stress factors mentioned above ultimately deprive plants' ability to make new sources of energy by inhibiting access to either water, sunlight, or oxygen, all necessary components of photosynthesis. If the immediate energy source is not supplied, plants resort to stored sources of energy locked in starch, oil, and proteins as seen under stress conditions. All 18 of the 20 naturally-occurring amino acids are precursors of substrates for gluconeogenesis to make glucose. If plants were engineered to be more efficient at performing gluconeogenesis, specific substrates along the metabolic pathways should be targeted for manipulation. Pyruvate, a substrate situated at a metabolic crossroad, can feed it into fermentation under anaerobic condition or cell respiration under aerobic condition. To divert pyruvate from entering anaerobic or aerobic respiration and, thus, depleting a viable source for glucose synthesis, pyruvate can be inducemetabolized into oxaloacetate by the over production of pyruvate carboxylase, the enzyme for the conversion. The abundance of oxaloacetate, a precursor for gluconeogenesis, may push the reactions forward. Pyruvate-oxaloacetate conversion also may stimulate the conversions of alanine, cysteine, glycine, serine, and threonine amino acids into pyruvate. The remaining 13 amino acids in FIG. 1 also may be stimulated to enter the cycle for the production of oxaloacetate if the accumulated substrate pool were used for phosphoenolpyruvate synthesis by PEPCK (phosphoenolpyruvate carboxylase).

When plants are subjected to various stress and growth-limiting conditions, metabolism is switched from energy storing (anabolism) to energy usage (catabolism). During periods of energy abundance, plants have evolved to store the excess energy in starch, oil, and proteins. When energy input is limited, the stored sources of energy can undergo metabolic interconversion into glucose via gluconeogenesis. Proteins are a major category of biomolecules in plants (corn kernels contain 9-10% proteins), and tapping into methods to convert proteins to sugars provide an added source of accessible substrates for ethanol production. Stress factors can mobilize the stored energy, and plants also can be engineered to actively take the gluconeogenic pathway. However, biomass buildup depends on the constant energy input without excessive external stress. To harvest the most possible sugars, plants may be allowed to build up biomass under nutrient-rich conditions then be subjected to stress just before harvesting, or plants can be engineered to grow normally while metabolizing sugars. How much economically-viable products we can extract from algal biomass depend on the available forms. A major hurdle in biofuel production is yield, and efforts to increase yield has focused on genetic engineering.

The current standard ethanol fermentation uses glucose sugar as feedstock, thus, limiting yield. The U.S. ethanol industry uses mostly corn as a feedstock, which contains 72% starch sugar that must be processed into glucose sugar for ethanol fermentation. Another source of glucose comes from cellulosic materials, which also have to be processed into glucose. Therefore, there still is a need for an alternative and improved production process of ethanol, which does not have all the drawbacks of existing processes. The engineered organisms herein described can use proteins in addition to sugars as carbon sources, therefore, increasing ethanol fermentation yield. Although the sugar glucose is the immediate energy source for cells, they can convert other nutrients like proteins, fats, and carbohydrates into glucose by the metabolic process called gluconeogenesis. The engineered organisms as described herein have enhanced gluconeogenesis pathways that can build up glucose, the feedstock for ethanol fermentation. This system has several advantages over the current ethanol fermentation system including increasing ethanol yield, using proteins and carbohydrates as sources of carbon, and making the clean biofuel production more economical.

DESCRIPTION OF THE INVENTION

The present invention relates to a scalable process for the production of an organic compound suitable as a biofuel or as chemical feedstock. The invention combines metabolic properties of chemoorganotrophic prokaryotes and is based on the use of recombinant heterotrophs with high rates of production of fermentative end product. The novelty of the invention is a) that a great variety of end products can be realized by the introduction of a single nucleic acid molecule encoding a specific protein and b) that its core chemical reactions use proteins and sugars as the carbon precursor to drive the production of organic compounds. The biochemical background of the invention is extensively described in example 1, and each aspect of the invention is extensively described below.

*Escherichia Coli*

In a first aspect, the invention provides a bacterium capable of expressing a nucleic acid molecule, wherein the expression of said nucleic acid molecule confers on the bacterium the ability increase production of a glycolytic intermediate and/or an organic compound.

In the context of the invention a bacterium is a *Escherichia coli* cell which is a heterotrophic unicellular prokaryote. This is a fast growing bacterium that can use amino acids as a carbon source. Its physiological traits are well-documented: it is able to survive and grow in a wide range of conditions.

A bacterium as defined herein is capable of increasing the production of a glycolytic intermediate and/or a organic compound as defined herein. A biochemical background of the bacterium of the invention is given in Example 1.

A bacterium as defined herein preferably comprises a nucleic acid molecule encoding a protein capable of increasing the production of glycolytic intermediates and/or an organic compound as defined herein. An organic compound is herein preferably defined as being a compound being more reduced than carbon dioxide. A bacterium is therefore capable of expressing a nucleic acid molecule as defined herein, whereby the expression of a nucleic acid molecule as defined herein confers on the bacterium the ability to increase production of glycolytic intermediates and/or an organic compound as defined herein. A glycolytic intermediate may be dihydroxyacetone-phosphate, glyceraldehyde-3-phosphate, 1,3-bis-phosphoglycerate, 2-phosphoglycerate, 3-phosphoglycerate, phospho-enol-pyruvate and pyruvate. Preferred glycolytic intermediates are pyruvate and glyceraldehyde-3-phosphate. The skilled person knows that the identity of the glycolytic intermediate converted into an organic product to be produced depends on the identity of the organic product to be produced.

Preferred organic products are selected from: a C1, C2, C3, C4, C5, or C6 alkanol, alkanediol, alkanone, alkene, or organic acid. Preferred alkanols are C2, C3 or C4 alkanols. More preferred are ethanol, propanol, butanol. A preferred alkanediol is 1,3-propanediol. A preferred alkanone is acetone. A preferred organic acid is D-lactate. A preferred alkene is ethylene.

A preferred glycolytic intermediate for the production of ethanol, propanol, butanol, acetone or D-lactate is pyruvate. A preferred glycolytic intermediate for the production of 1,3-propanediol is glyceraldehyde-3-phosphate. A preferred glycolytic intermediate for the production of ethylene is alpha-oxyglutarate "Increase production of glycolytic intermediates and/or an organic compound" preferably means that detectable amounts of an organic compound are detected in the culture of a bacterium as defined herein cultured for at least 1 day using a suitable assay for the organic compound.

All organic compounds produced are produced within the cell and may spontaneously diffuse into the culture broth. A preferred assay for said intermediates and alkanols, alkanones, alkanediols and organic acids is High Performance Liquid Chromatography (HPLC). A detectable amount for said glycolytic intermediates and alkanols, alkanones, alkanediols and organic acids is preferably at least 0.1 mM under said culture conditions and using said assay. Preferably, a detectable amount is at least 0.2 mM, 0.3 mM, 0.4 mM, or at least 0.5 mM.

Organic Compound

The nucleic acid molecule codes for a protein capable of increasing pyruvate and/or an organic compound, said protein comprises a polyglutamine. A preferred assay for an organic compound is HPLC. A detectable amount of an organic compound is preferably at least 0.1 mM under said culture conditions as defined earlier herein and using said assay. Therefore in this preferred embodiment, a bacterium comprises a nucleic acid molecule encoding a polyglutamine. Accordingly, this preferred embodiment relates to a bacterium capable of expressing the following nucleic acid molecule being represented by the nucleotide sequence, wherein the expression of this nucleotide sequence confers on the cell the ability to increase the production of pyruvate and/or an organic compound:

A nucleotide sequence encoding a polyglutamine, wherein said nucleotide sequence is x-CAA-x-CAG-x, in which CAA and CAG encode for glutamine, and "x" can be either CAA or CAG. Alternatively, said nucleic acid molecule and be interspersed with any codon and at any location. The polyglutamine stretch is at least 37 glutamines but can be as short as 5 glutamines or as long as thousands of glutamines. The polyglutamine tract can be located within any protein and at any location within a protein or can exist without any contiguous protein or amino acid.

Each nucleotide sequence encoding a protein as described herein may encode either a prokaryotic or a eukaryotic protein, i.e. a protein with an amino acid sequence that is identical to that of a protein that naturally occurs in a prokaryotic or eukaryotic organism. The present inventor has found that the ability of a protein as defined herein to confer to a bacterial cell the ability to increase the production of a glycolytic intermediate and/or an organic product does not depend so much on whether the protein is of prokaryotic or eukaryotic origin. Rather this depends on the relatedness (identity percentage) of the protein amino acid sequence or corresponding nucleotide sequence to CAA/CAG repeat sequence.

To this end, a nucleic acid construct may be constructed as described in e.g. Ordway et al., 1996, Biotechniques 21:609-612 or Chen et al., 2002, Methods in Molecular Biology, Volume 192, PCR Cloning Protocols, Humana Press, Inc. A bacterium may comprise a single but preferably comprises multiple copies of each nucleic acid construct. A nucleic acid construct may be maintained episomally and thus comprises a sequence for autonomous replication, such as an ARS sequence. Suitable episomal nucleic acid constructs may e.g. be based on the yeast 2.mu. or pKD1 (Fleer et al., 1991, Biotechnology 9:968-975) plasmids. Preferably, however, each nucleic acid construct is integrated in one or more copies into the genome of a bacterial cell. Integration into a bacterial cell's genome may occur at random by illegitimate recombination but preferably a nucleic acid construct is integrated into the bacterium cell's genome by homologous recombination as is well known in the art (U.S. Pat. No. 4,778,759). Homologous recombination occurs preferably at a neutral integration site. A neutral integration site is an integration which is not expected to be necessary for the production process of the invention, i.e for the growth and/or the production of an organic compound and/or an intermediary compound as defined herein. Accordingly, in a more preferred embodiment, a bacterial cell of the invention comprises a nucleic acid construct comprising a nucleic acid molecule, said nucleic acid molecule being represented by a nucleotide sequence, said nucleotide sequence being a coding sequence of a protein as identified herein. Said cyanobacterial cell is capable of expression of the protein. In an even more preferred embodiment, a nucleic acid molecule encoding a protein is operably linked to a promoter that causes sufficient expression of a corresponding nucleic acid molecule in a bacterium to confer to a bacterium the ability to increase production of a glycolytic intermediate and/or an organic product. A promoter is upstream of the expressing gene. Accordingly, in a further aspect, the invention also encompasses a nucleic acid construct as earlier outlined herein. Preferably, a nucleic acid construct comprises a nucleic acid molecule encoding a protein as earlier defined herein. Nucleic acid molecules encoding a protein have been all earlier defined herein.

A promoter that could be used to achieve the expression of a nucleic acid molecule coding for a protein as defined herein may be not native to a nucleic acid molecule coding for a protein to be expressed, i.e. a promoter that is heterologous to the nucleic acid molecule (coding sequence) to which it is operably linked. Although a promoter preferably is heterologous to a coding sequence to which it is operably linked, it is also preferred that a promoter is homologous, i.e. endogenous to a bacterium. Preferably, a heterologous promoter (to the nucleotide sequence) is capable of producing a higher steady state level of a transcript comprising a coding sequence (or is capable of producing more transcript molecules, i.e. mRNA molecules, per unit of time) than is a promoter that is native to a coding sequence. A suitable promoter in this context includes both constitutive and inducible natural promoters as well as engineered promoters. A promoter used in a bacterium cell of the invention may be modified, if desired, to affect its control characteristics.

Method

In a second aspect, the invention relates to a process of increasing the production of glycolytic intermediates and/or an organic compound as defined herein by using amino acid and/or sugar as carbon sources.

A bacterium, a glycolytic intermediate, an organic compound, a nucleic acid molecule, and a regulatory system have all earlier been defined herein.

In a process of the invention, amino acids and sugars in the culture medium are taken in and used by the bacterium as carbon sources or proteins and carbohydrates can be broken down into amino acids and sugars inside the cells. Usually a process is started with a culture (also named culture broth) of bacteria having an optical density measured at 660 nm of approximately 0.2 to 2.0 (OD.sub.660=0.2 to 2) as measured in any conventional spectrophotometer with a measuring path length of 1 cm. Usually the cell number in the culture doubles every 20 hours. In a preferred process, an organic compound is separated from the culture broth. This may be realized continuously with the production process or subsequently to it. Separation may be based on membrane technology and/or evaporation methods. Depending on the identity of the organic compound produced, the skilled person will know which separating method is the most appropriate.

General Definitions

Polyglutamine

Polyglutamine is herein defined as a tract of at least 30 to 40 Gln amino acids encoded by CAA/CAG repeats. The polyglutamine tract can be linked and/or interrupted by other amino acids. The location of the said polyglutamine tract may be located at the beginning, the end, or within a protein.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence than in its natural environment. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as earlier presented. Preferably the region of identity is greater than about 5 bp, more preferably the region of identity is greater than 10 bp. Preferably, two nucleic acid or polypeptides sequences are said to be homologous when they have more than 80% identity.

Heterologous

The term "heterologous" when used with respect to a nucleic acid (DNA or RNA) or protein refers to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Operably Linked

As used herein, the term "operably linked" refers to a linkage of polynucleotide elements (or coding sequences or nucleic acid sequence or nucleic acid molecule) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame.

Promoter

As used herein, the term "promoter" refers to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

Genetic Modifications

For overexpression of a protein in a host cell of the inventions as described above, as well as for additional genetic modification of a host cell, preferably bacteria, host cells are transformed with the nucleic acid construct of the invention by methods well known in the art. Such methods are e.g. known from standard handbooks, such as Sambrook and Russel (2001) "Molecular Cloning: A Laboratory Manual (3.sup.rd edition), Cold Spring Harbor Laboratory, Cold Spring Harbor Laboratory Press, or F. Ausubel et at, eds., "Current protocols in molecular biology", Green Publishing and Wiley Interscience, New York (1987). Methods for transformation and genetic modification of cyanobacterial cells are known from e.g. U.S. Pat. Nos. 6,699,696 or 4,778,759.

A promoter for use in a nucleic acid construct for overexpression of a protein in a cyanobacterial cell of the invention has been described above. Optionally, a selectable marker may be present in a nucleic acid construct. As used herein, the term "marker" refers to a gene encoding a trait or a phenotype which permits the selection of, or the screening for, a bacterial cell containing the marker. A marker gene may be an antibiotic resistance gene whereby the appropriate antibiotic can be used to select for transformed cells from among cells that are not transformed. Preferably however, a non-antibiotic resistance marker is used, such as an auxotrophic marker (URA3, TRP1, LEU2). In a preferred embodiment, a bacterial cell transformed with a nucleic acid construct is marker gene free. Methods for constructing recombinant marker gene free microbial host cells are disclosed in EP-A-0 635 574 and are based on the use of bidirectional markers. Alternatively, a screenable marker such as Green Fluorescent Protein, lacZ, luciferase, chloramphenicol acetyltransferase, beta-glucuronidase may be incorporated into a nucleic acid construct of the invention allowing to screen for transformed cells.

Optional further elements that may be present in a nucleic acid construct of the invention include, but are not limited to, one or more leader sequences, enhancers, integration factors, and/or reporter genes, intron sequences, centromers, telomers and/or matrix attachment (MAR) sequences. A nucleic acid construct of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3.sup.rd edition), Cold Spring Harbor Laboratory, Cold Spring Harbor Laboratory Press.

Methods for inactivation and gene disruption in bacterial cells are well known in the art (see e.g. Shestakov S V et al, (2002), Photosynthesis Research, 73: 279-284 and Nakamura Y et al, (1999), Nucleic Acids Res. 27:66-68).

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

EXAMPLES

Example 1

Biochemical Background of the *Escherichia coli* of the Invention

Figure 1:
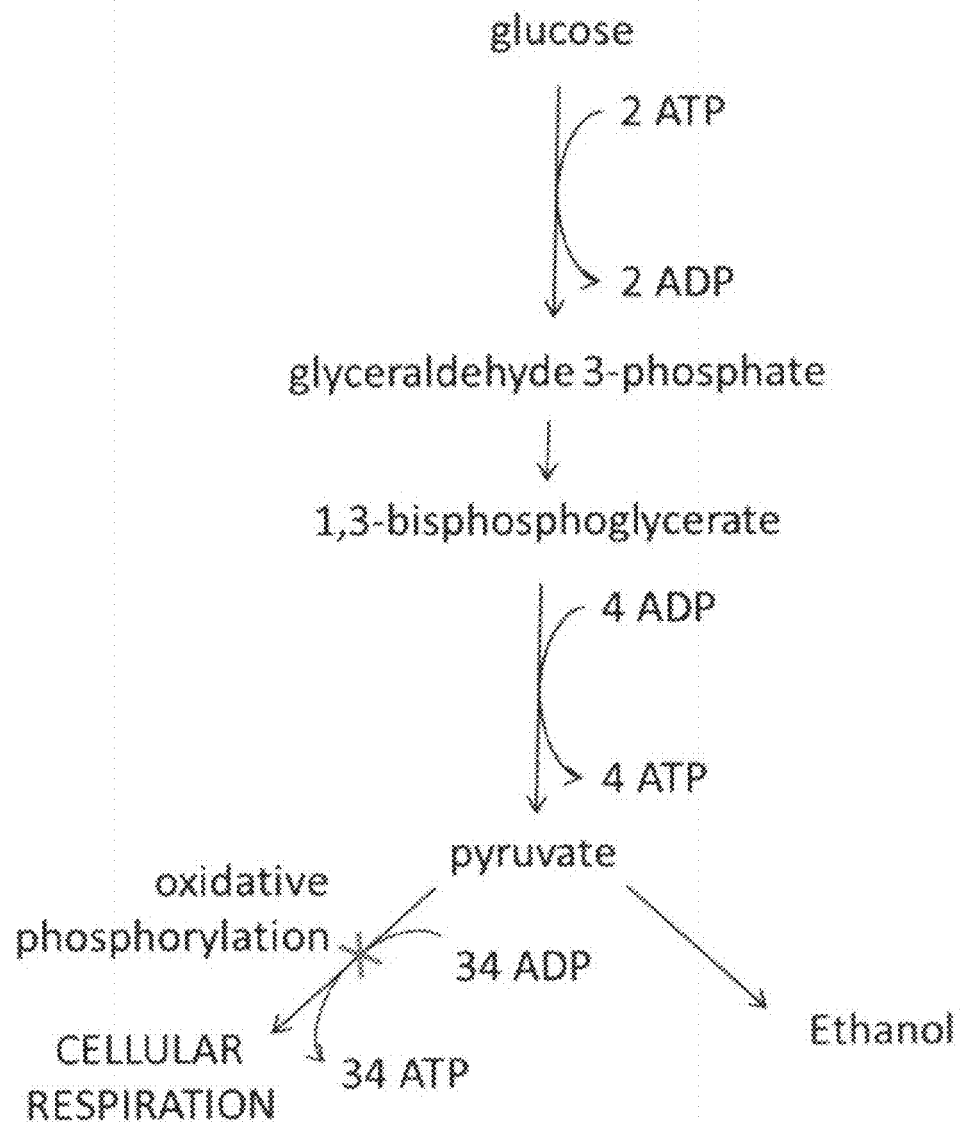
FIG. 1: Cellular Respiration and Ethanol Fermentation. The engineered cells have inhibited cell respiration but enhanced ethanol fermentation from pyruvate accumulation.

Glucose can be broken down into cellular energy (ATP) by two processes, Cellular Respiration and Fermentation. The *Escherichia coli* cell is engineered to shut down Cellular Respiration and, therefore, divert organic intermediate pyruvate into ethanol production (FIG. 1).

Figure 2:
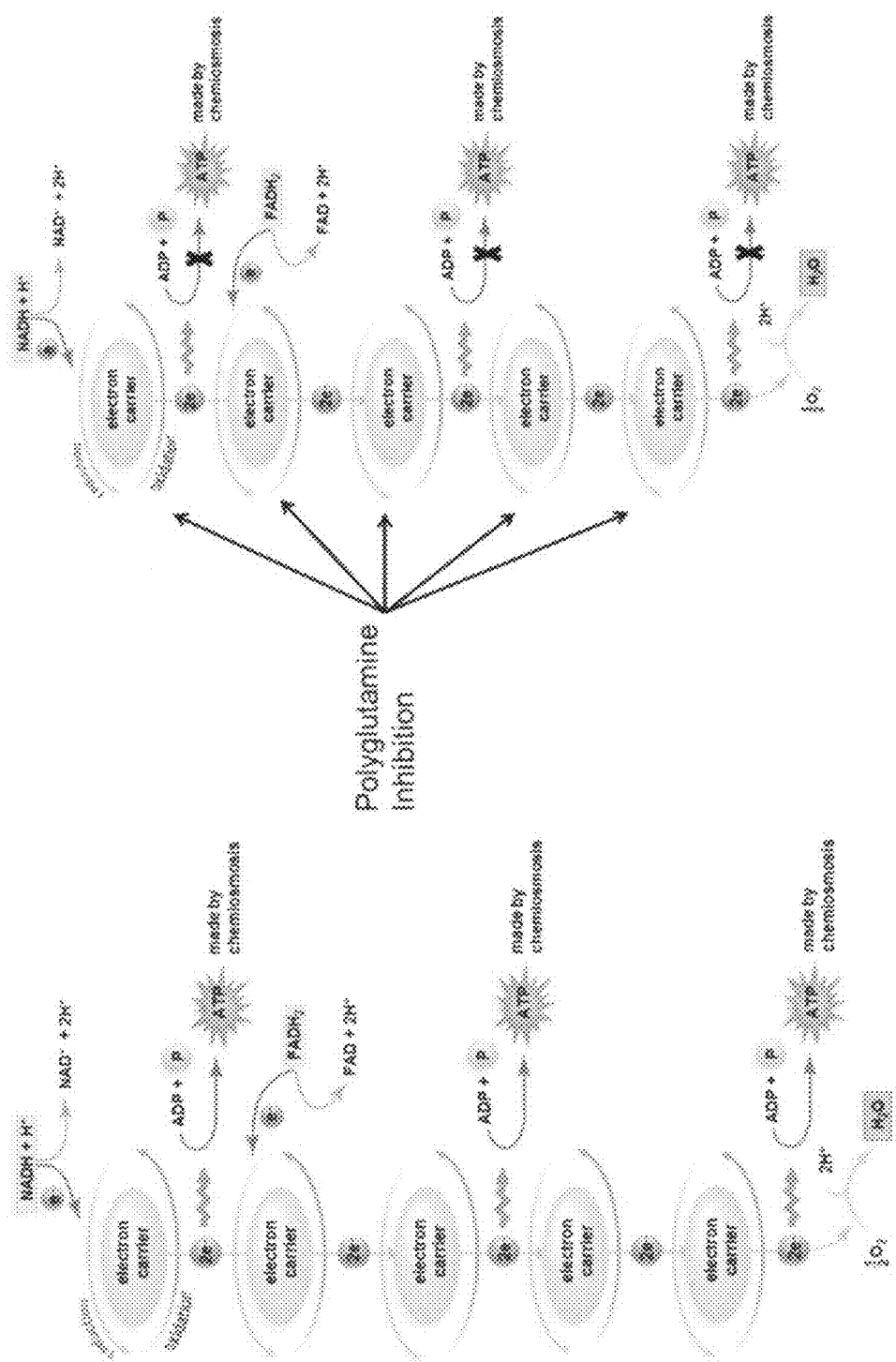
FIG. 2: Electron Transport Chain. Polyglutamine inhibits oxidative phosphorylation of ATP from electron transport reactions.

The bulk of the cellular energy ATP is made in the mitochondria during the Cellular Respiration phase of Electron Transport Chain. Polyglutamine protein has been shown to disrupt the functions of Electron Transport Chain as described by Shirendeb, U. et al. (Journal Hum. Mol. Genet. 2011 Apr. 1; 20(7):1438-55) (FIG. 2).

Cellular Respiration is the main energetic pathway in all cells. It consumes Oxygen and Glucose and yields $C_3$ compounds (e.g. pyruvate) and ATP:

$$O_2 + C_6H_{12}O_6 \rightarrow C_3 \text{ compounds} + ATP \quad (1)$$

Oxidative phosphorylation produces 32-34 ATP per glucose molecule, and therefore is the main phase of Cellular Respiration that sustains life through the cellular energy compound ATP.

Nature also sustains an entirely different mode of (microbial) life: Numerous bacterial and fungal species are able to conserve sufficient energy (as ATP) to proliferate by fermentation, in which they use so-called substrate level phosphorylation to generate their energy. This respiration-independent mode of energy conservation relies on metabolic pathways that result in redox neutral dissimilation of the energy source. The most abundant pathways have evolved with sugars (e.g. glucose) as energy source and therefore all have glycolysis in common:

$$\text{Glucose} \rightarrow \text{glyceraldehyde-P} \rightarrow \text{pyruvate} + \text{reducing power} \quad (2)$$

Redox neutrality is maintained by the generalized reaction:

$$\text{pyruvate} + \text{reducing power} \rightarrow \text{fermentation products} \quad (3)$$

Combining equations (2) and (3) in a redox-neutrality reaction that converts glucose into fermentation products, which are organic compounds as described herein.

Example 2

Description of the Expression System Used

Figure 3:
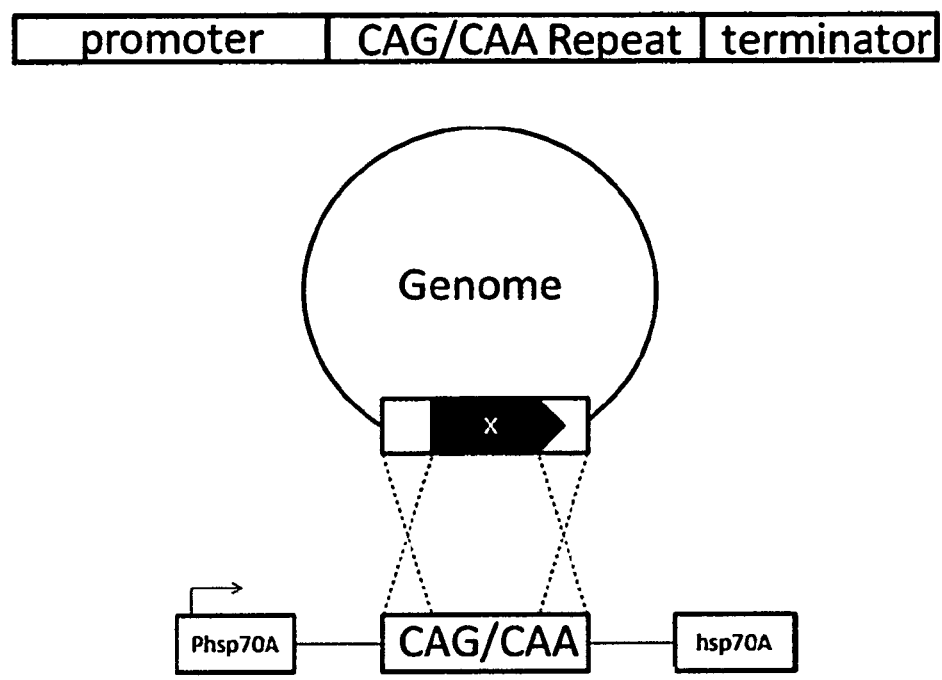
FIG. 3: Construction of a recombinant strain. CAG/CAA repeat sequence was synthesized according to Kim et al. (BioTechniques 38, 247-253). The CAG/CAA repeat DNA is linked to a promoter, which drives its expression. Homologous combination incorporates CAG/CAA repeat into the cell's genome.

The CAG/CAA-repeat sequence is linked downstream to a transcriptional promoter such as 17 or CMV that transcribe the DNA repeat sequence into the coding mRNA sequence, which translates into the polyglutamine protein. The genetic cassette can be used to transform a cell transiently or stably by homologous recombination that incorporates the cassette into the cell's genome (FIG. 3).

Example 3

Amino Acids as Carbon Source

Figure 4:
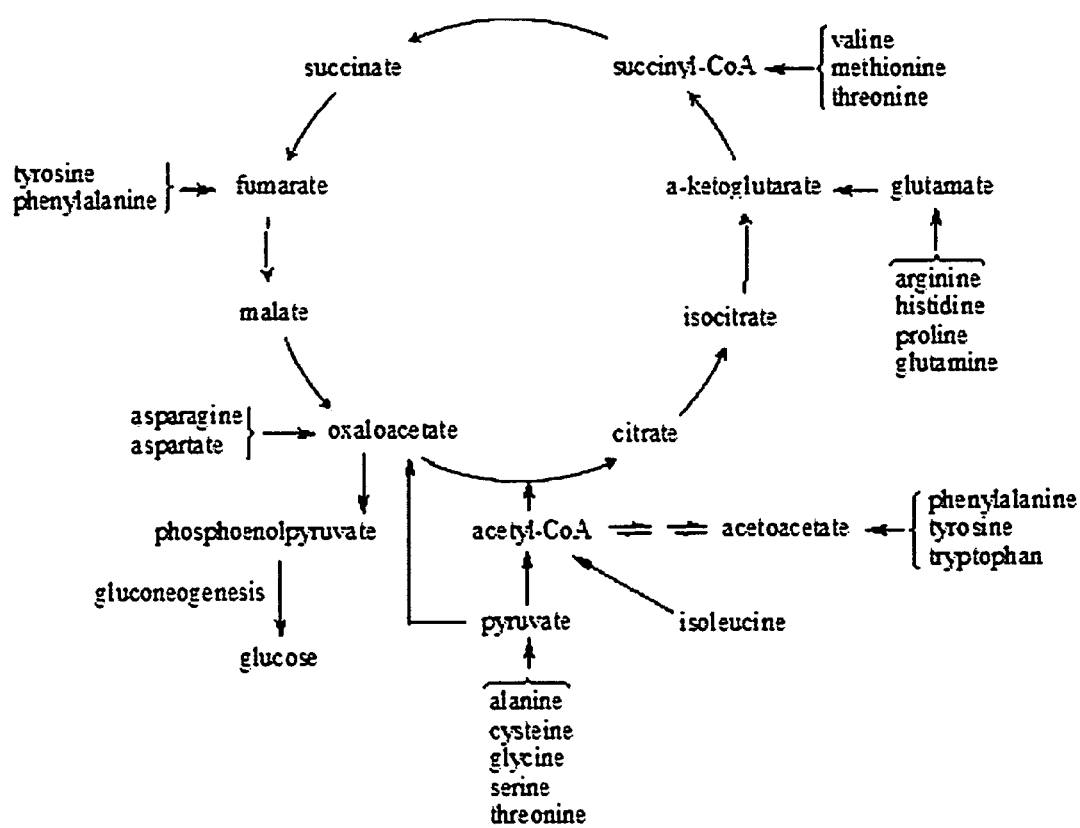
FIG. 4: Gluconeogenesis. Amino acids are carbon sources that can be converted into glucose by cells such as *Escherichia coli* as described by Sezonov et al. (Journal of Bacteriology. 189(23), 8746-8749).

*Escherichia coli* is able to use amino acids as a carbon source by converting them into glucose by the biochemical process of gluconeogenesis (FIG. 4). This is described by Sezonov et al. (Journal of Bacteriology. 189(23), 8746-8749). Glucose is then used for fermentation in the engineered bacterium.

TABLE 1 list of all primers used

| | | |
|---|---|---|
| CAG-REPEAT 1 | Forward | AATTCGAGTCGCGCG(CTG)7GCGCGACTCG |
| | Reverse | GATCCGAGTCGCGC(CAG)7CGCGCGACTCG |
| ECONI 2 | Forward | GAATTCGAGTCCTGGGGAGGACTCGGATCC |
| | Reverse | GGATCCGAGTCCTCCCCCAGGACTCGAATTC |

References

[1] Kim S H., Cai L., Pytlos M., Edwards S., Sinden R. (2005) Generation of long tracts of disease-associated DNA repeats. BioTechniques 38, 247-253.

[2] Hongmin W., Lim P., Karbowski M., Monteiro M. (2009) Effects of overexpression of Huntingtin proteins on mitochondrial integrity. Hum. Mol. Gen. 18(4), 737-752.

[3] Sezonov G., Jose-Petit D., D'Ari R. (2007) *Escherichia coli* physiology in Luria-Bertani broth. Journal of Bacteriology. 189(23), 8746-8749.

The invention claimed is:

1. A process for increasing the production of pyruvate and ethanol from a carbon substrate of sugar or protein by a bacterial cell in culture, wherein the bacterial cell comprises a nucleic acid having a CAG/CAA repeat that encodes a polyglutamine protein with at least 37 glutamine residues and expression of the nucleic acid gives the bacterial cell the ability to increase the production of pyruvate and ethanol.

2. A process according to claim 1, wherein the nucleic acid comprised in the bacterial cell is integrated into its genome.

3. A process according to claim 1, wherein the nucleic acid comprised in the cell is carried within a plasmid.

4. A process according to claim 1, wherein the ethanol is separated from the culture.

5. A process according to claim 1, wherein the bacterial cell is *Escherichia coli*.

6. A process according to claim 2, wherein the nucleic acid is integrated into the genome by homologous recombination.

* * * * *

SEQUENCE LISTING

<160> NUMBER OF SEQ ID NOS: 1

<210> SEQ ID NO 1
<211> LENGTH: 38
<212> TYPE: PRT
<213> ORGANISM: Homo sapiens

```
<300> PUBLICATION INFORMATION:
<301> AUTHORS: Hongmin W., Lim P., Karbowski M., Monteiro M.
<302> TITLE: Effects of overexpression of Huntingtin proteins on
       mitochondrial integrity
<303> JOURNAL: Human Molecular Genetics
<304> VOLUME: 18
<305> ISSUE: 4
<306> PAGES: 737-752
<307> DATE: 2009
<313> RELEVANT RESIDUES IN SEQ ID NO: (1)..(38)

<400> SEQUENCE: 1

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln
        35
```